United States Patent
Nan et al.

(10) Patent No.: US 10,766,889 B2
(45) Date of Patent: Sep. 8, 2020

(54) ARYL-2,2'-TANDEM BISTHIAZOLE COMPOUND AND PREPARATION METHOD AND USE THEREOF

(71) Applicant: SHANGHAI INSTITUTE OF MATERIA MEDICA, CHINESE ACADEMY OF SCIENCES, Pudong, Shanghai (CN)

(72) Inventors: Fajun Nan, Shanghai (CN); Jia Li, Shanghai (CN); Jian Ding, Shanghai (CN); Meiyu Geng, Shanghai (CN); Yangming Zhang, Shanghai (CN); Yi Chen, Shanghai (CN); Yubo Zhou, Shanghai (CN); Chaojun Gong, Shanghai (CN); Mingbo Su, Shanghai (CN); Anhui Gao, Shanghai (CN)

(73) Assignee: Shanghai Institute of Materia Medica, Chinese Academy of Sciences, Shanghai (CN)

( * ) Notice: Subject to any disclaimer, the term of this patent is extended or adjusted under 35 U.S.C. 154(b) by 0 days.

(21) Appl. No.: 16/329,336

(22) PCT Filed: Aug. 24, 2017

(86) PCT No.: PCT/CN2017/098883
§ 371 (c)(1),
(2) Date: Feb. 28, 2019

(87) PCT Pub. No.: WO2018/041004
PCT Pub. Date: Mar. 8, 2018

(65) Prior Publication Data
US 2019/0211005 A1 Jul. 11, 2019

(30) Foreign Application Priority Data

Aug. 31, 2016 (CN) .................. 2016 1 07863928

(51) Int. Cl.

| | |
|---|---|
| *C07D 277/56* | (2006.01) |
| *C07D 277/60* | (2006.01) |
| *C07D 417/04* | (2006.01) |
| *A61P 35/02* | (2006.01) |
| *A61K 31/427* | (2006.01) |
| *A61P 35/00* | (2006.01) |

(52) U.S. Cl.
CPC .......... *C07D 417/04* (2013.01); *A61K 31/427* (2013.01); *A61P 35/00* (2018.01); *A61P 35/02* (2018.01); *C07D 277/56* (2013.01); *C07D 277/60* (2013.01); *Y02P 20/55* (2015.11)

(58) Field of Classification Search
CPC ... C07D 277/56; C07D 277/60; C07D 417/04
See application file for complete search history.

(56) References Cited

U.S. PATENT DOCUMENTS

| | | | | |
|---|---|---|---|---|
| 9,216,962 | B2 * | 12/2015 | Nan ..................... | C07D 277/56 |
| 2014/0148600 | A1 * | 5/2014 | Nan ..................... | C07D 277/56 |
| | | | | 546/209 |

FOREIGN PATENT DOCUMENTS

| | | |
|---|---|---|
| CN | 102775368 A | 11/2012 |
| WO | 2012152208 A1 | 11/2012 |

OTHER PUBLICATIONS

Benedetti et al., "Targeting Histone Deacetylases in Diseases: Where Are We?" Antioxidants & Redox Signaling, vol. 23, No. 1, pp. 99-126 (2015).

Delcuve et al., "Roles of histone deacetylases in epigenetic regulation: emerging paradigms from studies with inhibitors," Clinical Epigenetics, vol. 4, No. 5, pp. 1-13 (2012).

International Preliminary Report on Patentability dated Mar. 5, 2019 in International Application No. PCT/CN2017/098883; dated Mar. 14, 2019.

International Search Report dated Nov. 15, 2017 in International Application No. PCT/CN2017/098883.

* cited by examiner

*Primary Examiner* — Laura L Stockton
(74) *Attorney, Agent, or Firm* — Panitch Schwarze Belisario & Nadel LLP

(57) ABSTRACT

The invention describes an aryl-2,2'-tandem bisthiazole compound and a preparation method and the use thereof. In particular, disclosed in the present invention are an aryl-2, 2'-tandem bisthiazole compound with the structure as shown in general formula I and the preparation method thereof and use thereof as a histone deacetylase inhibitor in the preparation of antitumor drugs.

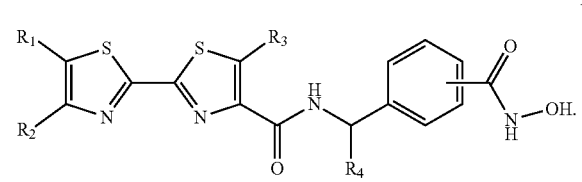

19 Claims, No Drawings

ARYL-2,2'-TANDEM BISTHIAZOLE COMPOUND AND PREPARATION METHOD AND USE THEREOF

CROSS-REFERENCE TO RELATED APPLICATION

This application is a Section 371 of International Application No. PCT/CN2017/098883, filed Aug. 24, 2017, the disclosure of which is incorporated herein by reference in its entirety, which was published in the Chinese language on Mar. 8, 2018, under International Publication No. WO 2018/041004 A1, which claims priority under 35 U.S.C. § 119(b) to Chinese Application No. 201610786392.8, filed Aug. 31, 2016.

FIELD OF THE INVENTION

The present invention relates to a class of bisthiazole compounds, the preparation method and use thereof, and more particularly to a class of aryl-2,2'-tandem bithiazole compounds, a process for the preparation thereof, and the use as histone deacetylase inhibitors in the preparation of antitumor drugs.

BACKGROUND OF THE INVENTION

Epigenetics refers to the study of reversible, heritable changes in gene function without changes in nuclear DNA sequences. DNA methylation and post-transcriptional modification of histones are the two most common mechanisms of epigenetic regulation. Wherein histone acetylation modification is the most widely studied, which is regulated by the activity of histone acetyltransferase (HAT) and histone deacetylase (HDAC). (*Clinical epigenetics* 2012, 4 (1), 5).

Abnormal expression or mutation of HDAC may lead to imbalance of histone acetylation, lead to changes in chromatin structure, inhibit cell growth, differentiation, and apoptosis-related gene expression, and help to improve tumor tolerance to chemotherapy, promote tumor cell proliferation, migration and angiogenesis, and at the same time inhibit the differentiation and apoptosis of tumor cells, thereby leading to tumorigenesis. (*ANTIOXIDANTS & REDOX SIGNALING* 2015, 23 (1), 99-126). HDAC inhibitors can achieve targeted treatment of tumors by remodeling epigenetic functions.

According to the latest Thompson Reuters Integrity data, more than 1,000 HDAC is are in different stages of drug development. Five of them have been approved to come into the market, which are: the first HDAC inhibitor vorinostat (SAHA, Zolinza) approved by the FDA in October in 2006, romidepsin (depsipeptide, FK228) from Gloucester, panobinostat (LBH589, Farydak) from Novartis, Belinostat from Spectrum, and Chidamide (Epidaza) from Shenzhen Micro Core company.

The inventors disclosed a class of bithiazole compounds (WO2012152208) which can be used as an HDAC inhibitor for the development of anti-tumor and multiple sclerosis drugs. Among them, the compound CFH367-C (bexanostat) showed good enzyme activity and tumor cell proliferation inhibitory activity ($IC_{50}$<400 nM).

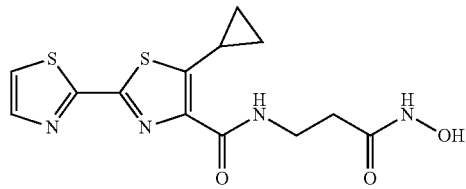

CFH367-C

Also, 201410136196.7 disclosed a class of bithiazole HDAC inhibitors. These compounds not only have better inhibitory activity against HDAC ($IC_{50}$=30 nM), but also have stronger inhibitory activity against multiple myeloma cell proliferation ($IC_{50}$ can reach up to 100 nM level), and the therapeutic effect on clinical symptoms of EAE mice is obviously better than CFH367-C. However, subsequent studies have shown that the metabolic properties of this class of compounds are poor, in which the oral bioavailability of the representative compound GCJ403 is only 14.7%.

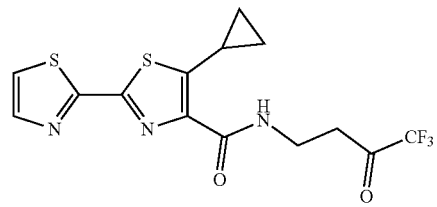

GCJ403

Therefore, it is very meaningful to develop an HDAC inhibitor with good metabolic properties.

SUMMARY OF THE INVENTION

One object of the present invention is to provide a novel class of aryl-2,2'-tandem bithiazole compounds or optical isomers thereof, or pharmaceutically acceptable salts thereof, which can be used in the preparation of HDAC inhibitors.

Another object of the present invention is to provide a preparation method of the above compounds.

Another object of the present invention is to provide the use of the above compounds in the preparation of histone deacetylase inhibitor medicine or the use thereof in the preparation of an antitumor drug.

Another object of the present invention is to provide a pharmaceutical composition comprising therapeutically effective amount of the above compound, and a pharmaceutically acceptable carrier.

In the first aspect of the invention, an aryl-2,2'-tandem bithiazole compound of the formula I or an optical isomer thereof, or a pharmaceutically acceptable salt thereof is provided;

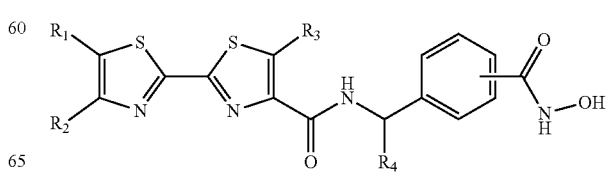

Formula I wherein,

R₁ and R₂ are each independently one of the following groups: H, $C_1$-$C_6$ alkyl, $C_2$-$C_6$ alkenyl, $C_2$-$C_6$ alkynyl, $C_3$-$C_6$ cycloalkyl, $C_5$-$C_{10}$ aryl; or R₁ and R₂ together with the carbon atom to which they are attached form a 5-7 membered saturated or partially saturated ring;

R₃ is one of the following groups: H, $C_1$-$C_6$ alkyl, $C_3$-$C_6$ cycloalkyl, $C_2$-$C_6$ alkenyl, $C_2$-$C_6$ alkynyl, $C_5$-$C_{10}$ aryl;

R₄ is one of the following groups: H, $C_1$-$C_6$ alkyl, $C_3$-$C_6$ cycloalkyl, $C_2$-$C_6$ alkenyl, $C_2$-$C_6$ alkynyl, $C_5$-$C_{10}$ aryl;

the above groups are unsubstituted or substituted with one or more groups selected from the group consisting of halogen, $C_1$-$C_6$ alkyl, halogenated $C_1$-$C_6$ alkyl, $C_2$-$C_6$ alkenyl, $C_2$-$C_6$ alkynyl, $C_1$-$C_6$ alkoxy, halogenated $C_1$-$C_6$ alkoxy, $C_3$-$C_6$ cycloalkyl, $C_5$-$C_{10}$ aryl.

In another preferred embodiment, the compound is a compound of the formula II-2, wherein R₁, R₂, R₃ and R₄ are as defined above;

Formula II-2

In another preferred embodiment, R₁ and R₂ are each independently H, $C_1$-$C_6$ alkyl, $C_6$-$C_{10}$ aryl; or R₁ and R₂ together with the carbon atom to which they are attached form a 5, 6 or 7 membered partially saturated ring.

In another preferred embodiment, R₁ and R₂ are each independently H or phenyl; the phenyl is unsubstituted or substituted by one or more groups selected from the group consisting of halogen, $C_1$-$C_6$ alkyl, halo $C_1$-$C_6$ alkyl, $C_1$-$C_6$ alkoxy, halo $C_1$-$C_6$ alkoxy, $C_3$-$C_6$ cycloalkyl;

In another preferred embodiment, R₁ is phenyl, and R₂ is H.

In another preferred embodiment, R₃ is $C_1$-$C_4$ alkyl, $C_6$-$C_{10}$ aryl substituted $C_1$-$C_4$ alkyl or $C_3$-$C_6$ cycloalkyl.

In another preferred embodiment, R₃ is $C_1$-$C_4$ alkyl, benzyl, or cyclopropyl.

In another preferred embodiment, R₃ is cyclopropyl.

In another preferred embodiment, R₄ is $C_1$-$C_6$ alkyl.

In another preferred embodiment, R₄ is S configuration $C_1$-$C_6$ alkyl.

In another preferred embodiment, R₄ is S configuration methyl.

In another preferred embodiment, the compound is selected from the group consisting of:

H01

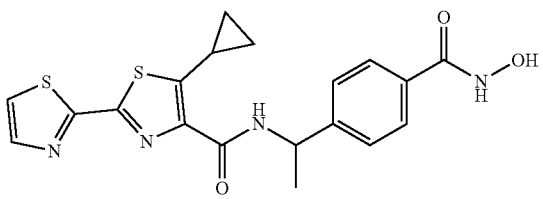 [SMILES: CC(NC(=O)c1nc(-c2nccs2)sc1C1CC1)c1ccc(C(=O)NO)cc1]

-continued

H02

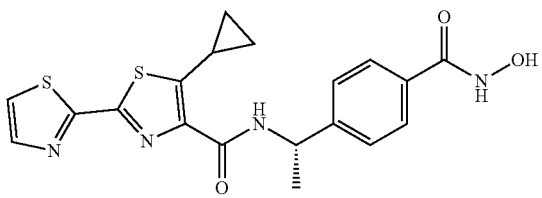 [SMILES: C[C@H](NC(=O)c1nc(-c2nccs2)sc1C1CC1)c1ccc(C(=O)NO)cc1]

H03

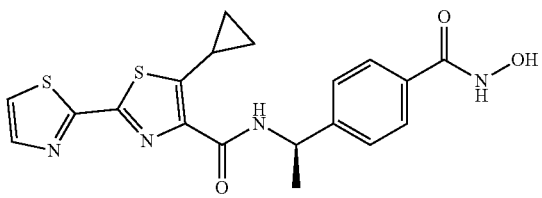 [SMILES: C[C@@H](NC(=O)c1nc(-c2nccs2)sc1C1CC1)c1ccc(C(=O)NO)cc1]

H04

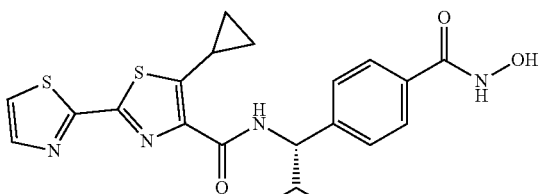

H05

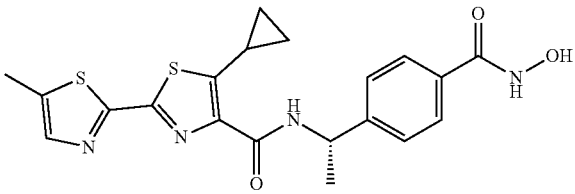 [SMILES: Cc1cnc(-c2nc(C(=O)N[C@@H](C)c3ccc(C(=O)NO)cc3)c(C3CC3)s2)s1]

H06

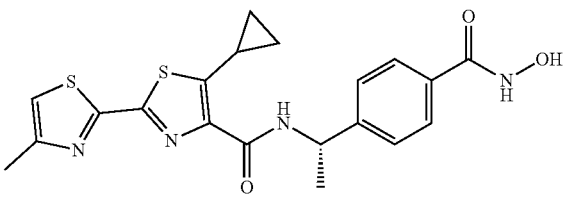 [SMILES: Cc1csc(-c2nc(C(=O)N[C@@H](C)c3ccc(C(=O)NO)cc3)c(C3CC3)s2)n1]

H07

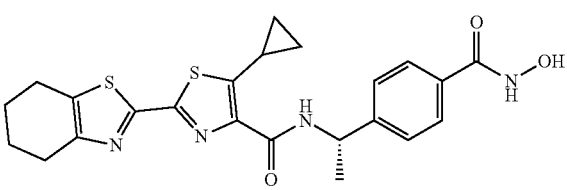 [SMILES: C[C@H](NC(=O)c1nc(-c2nc3c(s2)CCCC3)sc1C1CC1)c1ccc(C(=O)NO)cc1]

H08

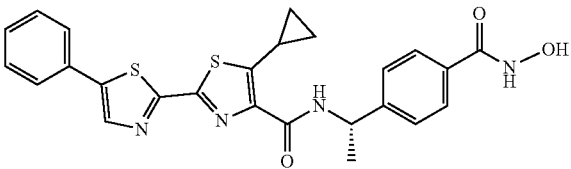

-continued

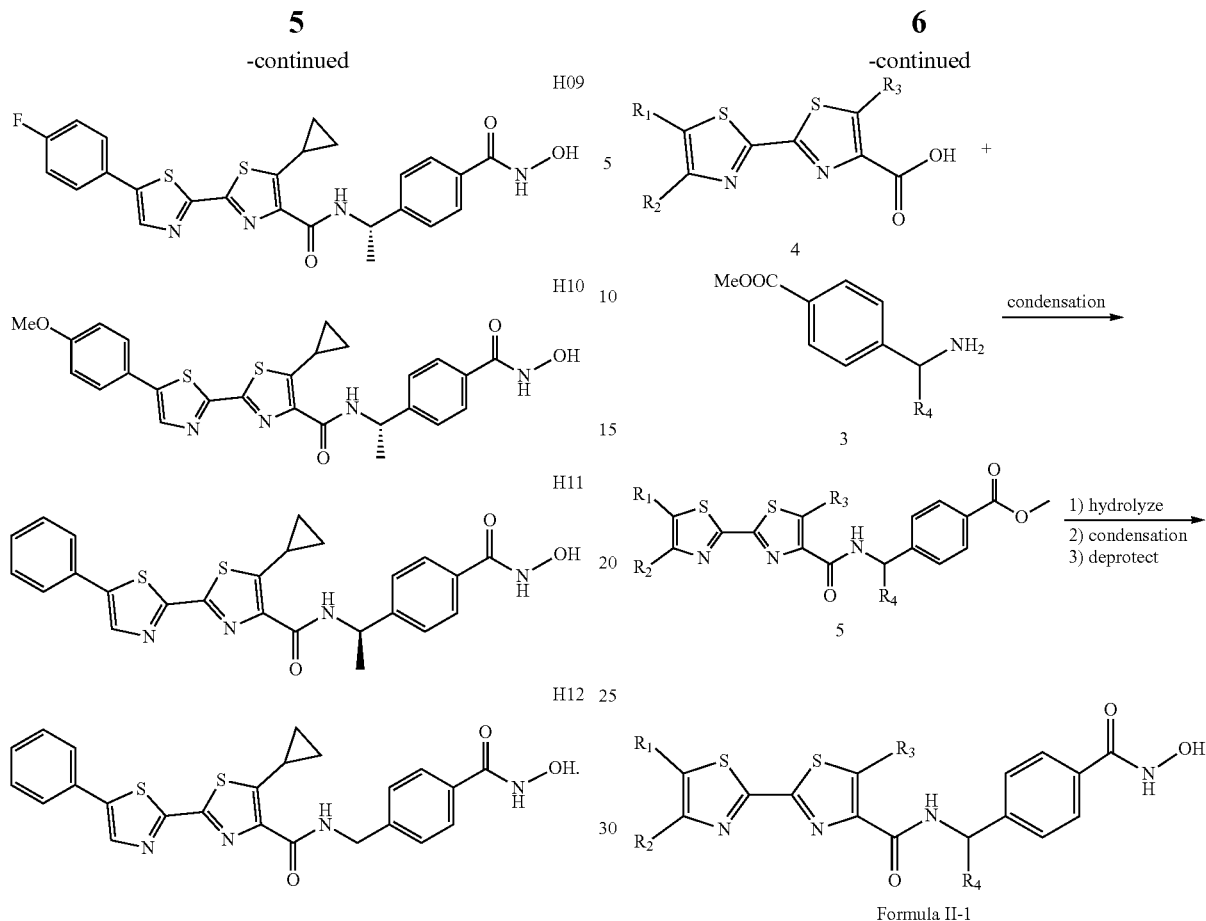

In the second aspect of the present invention, a method for producing the compound, or an optical isomer thereof, or a pharmaceutically acceptable salt thereof of the first aspect is provided, The method is with a route shown in the route I,

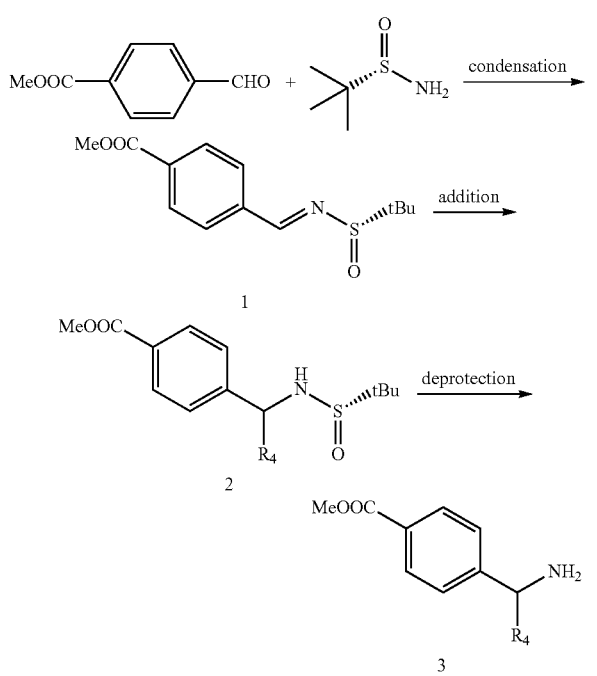

wherein, $R_1$, $R_2$, $R_3$ and $R_4$ are defined as above, except that $R_4$ is other than H;

comprising steps:

(1) condensing methyl 4-acetylbenzoate with tert-butyl sulfenamide to form tert-butyl sulfoximine 1;

(2) adding tert-butyl sulfinimide 1 and Grignard reagent to form tert-butyl sulfenamide 2;

(3) deprotecting tert-butyl sulfinamide 2 to form amine 3;

(4) condensation reacting amine 3 with acid 4 to form methyl ester 5;

(5) after hydrolysis reacting methyl ester 5 with alkali, exchanging with a hydroxylamine protected by a protecting group, and finally removing the protecting group to form a compound of the formula II-1; or the method is with a route shown in the route II:

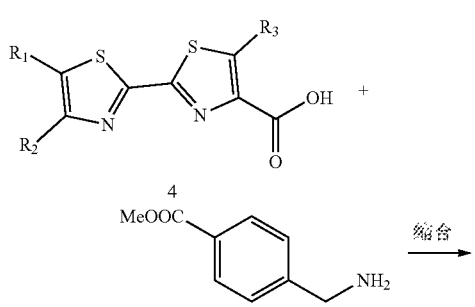

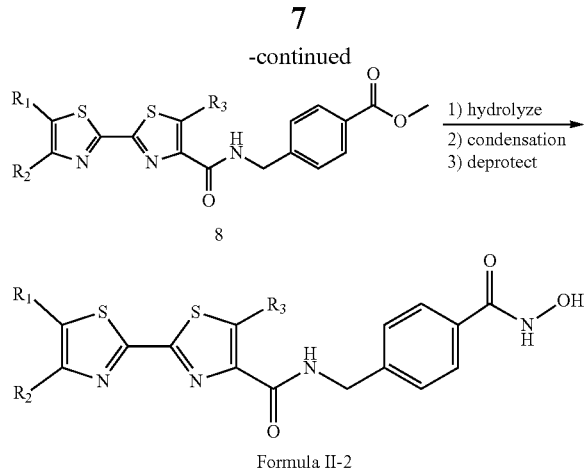

Formula II-2 wherein, $R_1$, $R_2$, and $R_3$ are defined as above;
comprising steps:
(i) condensation reacting acid 4 with methyl 4-aminomethylbenzoate to form methyl ester 8;
(ii) after hydrolysis reacting methyl ester 8 with alkali, reacting with a hydroxylamine protected by a protecting group, and finally removing the protecting group to form a compound of the formula II-2.

In the third aspect of the present invention, a use of the compound, or an optical isomer thereof, or a pharmaceutically acceptable salt thereof of the first aspect for the preparation of a histone deacetylase inhibitor is provided.

In the fourth aspect of the present invention, a use of the compound, or an optical isomer thereof, or a pharmaceutically acceptable salt thereof of the first aspect in the preparation of antitumor medicine or tumor cells inhibiting medicine is provided.

In another preferred embodiment, the tumor is multiple myeloma, colon cancer, lung cancer, liver cancer, breast cancer, ovarian cancer, pancreatic cancer, rectal cancer, gastric cancer, lymphoma, leukemia.

In another preferred embodiment, the tumor cells are multiple myeloma cells, colon cancer cells, lung cancer cells, embryo lung cells, liver cancer cells, breast cancer cells, ovarian cancer cells, pancreatic cancer cells, rectal cancer cells, gastric cancer cells, lymphoma cells or leukemia cells.

In another preferred embodiment, the lymphoma is B cell lymphoma, T cell lymphoma or the like.

In another preferred embodiment, the T cell lymphoma is cutaneous T cell lymphoma, peripheral T cell lymphoma, or the like.

In the fifth aspect of the invention, a pharmaceutical composition is provided, wherein the pharmaceutical composition comprises a therapeutically effective amount of a compound or an optical isomer thereof, or a pharmaceutically acceptable salt thereof of the first aspect of the invention, and pharmaceutically acceptable carrier.

It should be understood that, in the present invention, each of the technical features specifically described above and below (such as those in the Examples) can be combined with each other, thereby constituting new or preferred technical solutions which need not be specified again herein.

DESCRIPTION OF THE DRAWINGS

FIG. 1 shows the pharmacodynamic results of compound H08 in human myeloma RPMI 8226 NOD/SCID mouse xenografts.

EMBODIMENTS FOR CARRYING OUT THE INVENTION

Through extensive and in-depth research, the inventors have found that when an aryl group is introduced into a thiazole ring, and the linking position is changed from alkane to phenyl group or benzyl group, the obtained aryl-2,2'-tandem bithiazole compound would possess significantly improved in vitro and in vivo activity than the existing compounds (such as CFH367-C). Also, the oral absorption characteristics are much more improved than the existing compounds (such as GCJ403) (the oral bioavailability of mice can reach up to 34.4%), and it is of better safety than the existing compounds such as CFH367-C, and therefore has better development prospects. The inventor has completed the present invention on this basis.

Terms

As used herein, "$C_1$-$C_6$ alkyl" refers to a straight or branched alkyl having from 1 to 6 carbon atoms, such as methyl, ethyl, propyl, isopropyl, butyl, isobutyl, tert-butyl, pentyl, hexyl, and the like.

As used herein, "$C_2$-$C_6$ alkenyl" refers to a straight or branched alkenyl having 2 to 6 carbon atoms, such as ethenyl, propenyl, butenyl, isobutenyl, pentenyl, hexenyl, and the like.

As used herein, "$C_2$-$C_6$ alkynyl" refers to a straight or branched alkynyl having 2 to 6 carbon atoms, such as ethynyl, propynyl, butynyl, pentynyl, hexynyl, and the like.

As used herein, "$C_3$-$C_6$ cycloalkyl" refers to a cycloalkyl group having 3 to 6 carbon atoms such as cyclopropyl, cyclobutyl, cyclopentyl, cyclohexyl, and the like.

As used herein, "$C_5$-$C_{10}$ aryl" refers to an aryl group having 5 to 10 carbon atoms, such as phenyl group, naphthyl group, and the like.

As used herein, "5-7 membered saturated or partially saturated ring" refers to a saturated or partially saturated ring having 5 to 7 ring atoms, such as hexacyclic ring containing 1-2 double bonds.

As used herein, "$C_1$-$C_6$ alkoxy" refers to straight or branched alkoxy having 1 to 6 carbon atoms, such as methoxy, ethoxy, propoxy, isopropoxy, butoxy, isobutoxy, tert-butoxy, pentyloxy, hexyloxy, and the like.

As used herein, "halogenate" refers to fluorinate, chlorinate, brominate, iodinate.

The Main Advantages of the Present Invention are

The inventors studied the structure-activity relationship of such bithiazole HDAC inhibitors, and found that the activity of HDAC subtypes increased to a certain extent after the linker was changed from a long fat chain to a benzyl group; the introduction of a phenyl group at the 5-position of the thiazole made the inhibitory activity of the compound H12 to HDAC1, 3, 6 increase by several times, and the $IC_{50}$ was about 6-10 nM; and the compound H08 obtained by the addition of a chiral S-methyl substitutent at benzyl position further improved the HDAC enzyme inhibitory activity, of which the $IC_{50}$ can reach 2-3 nM, which was much more improved than bexanostat.

The compound provided by the present invention has a significantly enhanced inhibitory effect on the proliferation of human multiple myeloma cell line RPMI 8226 compared with the existing compounds (such as beoxinostat). For example, IC$_{50}$ of compound H08 can reach 8 nM, of which the activity is higher than that those known HDAC inhibitors.

More importantly, the efficacy of the compounds provided by the present invention in an animal model of multiple myeloma is also better compared to existing compounds such as bexanostat. For example, after continuously oral administrate compound H08 50 mg/kg for three weeks, there would be a therapeutic effect on human myeloma RPMI 8226 NOD/SCID mouse xenografts, and the proliferation of mouse xenografts would be effectively inhibited. The relative tumor growth rate T/C is 34.49%, which was equivalent to the oral administration of bexanostat 100 mg/kg bid test group (T/C was 30.40%). There was no change in body weight of the mice during the experiment, which further indicated the safety of the compound H08.

Furthermore, the compounds provided by the present invention not only greatly improves the in vitro and in vivo activity, but also improves the oral absorption characteristics. The preliminary metabolic experiments shows that the oral bioavailability of the compound H08 mice can reach 34.4%.

In summary, the activity of the compound provided by the present invention has been greatly improved, and the compound is of lower toxicity, and better oral absorption property, thus having better development prospect.

Further, the compound of the present invention has excellent inhibitory activity against various solid tumors (e.g., breast cancer, liver cancer, lung cancer, stomach cancer, colon cancer, lymphoma, leukemia, etc.).

The present invention will be further illustrated below with reference to the specific examples. It should be understood that these examples are only to illustrate the invention but not to limit the scope of the invention. The experimental methods with no specific conditions described in the following examples are generally performed under the conventional conditions, or according to the manufacturer's instructions. Unless indicated otherwise, parts and percentage are calculated by weight.

Compound Preparation Examples

In the following preparation examples, NMR was measured by Mercury-Vx 300M instrument manufactured by Varian, and NMR calibrations were: δ H 7.26 ppm (CDCl$_3$), 2.50 ppm (DMSO-d$_6$), 3.31 ppm (CD$_3$OD); all solvents were analytically pure reagents which were generally used without treatment. The anhydrous solvent was dried by standard methods. Other reagents were generally purchased from reagent companies such as Sinopharm Chemical Reagent Co., Ltd., Shaoyuan Chemical Technology (Shanghai) Co., Ltd., Jill Biochemical (Shanghai) Co., Ltd., Shenzhen Myrill Chemical Technology Co., reagent companies such as Aldrich, Alfa-Aesar, Acros, Fluka, Merck, TCI or Lancaster etc., while some of the reagents were purchased from the manufacturer. Unless otherwise specified, these reagents were used without treatment. Self-made reagents were generally subjected to NMR to determine their structure and approximate purity prior to use. TLC thin layer chromatography silica gel plate was produced by the Shandong Yantai Huiyou Silicone Development Co., Ltd., model HSGF 254; normal phase column chromatography silica gel used for the compounds purification was produced by the Qingdao Marine Chemical Factory factory production, model zcx-11, 200-300 mesh.

Preparation Example 1 (Compound No. H08-Route 1)

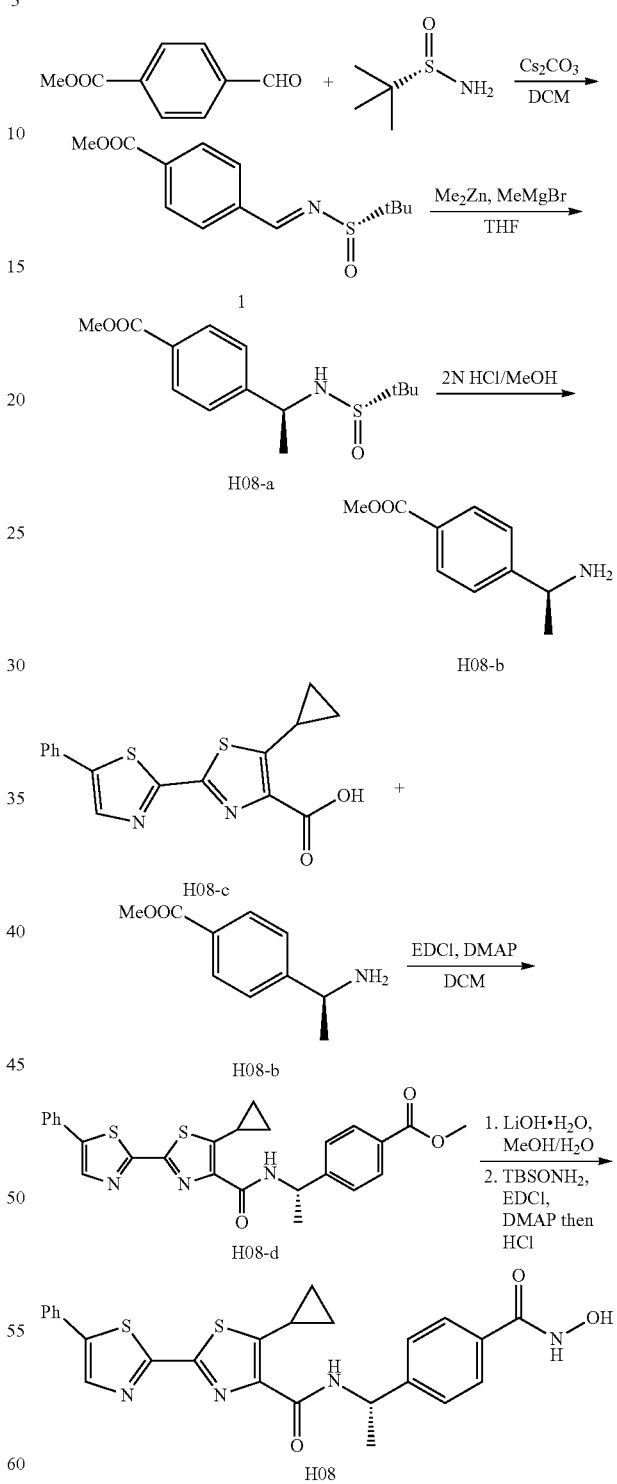

Methyl 4-formylbenzoate (5 g, 30.5 mmol) was dissolved in 150 mL dichloromethane, and S-tert-butyl sulfenamide (4.43 g, 36.6 mmol) and cesium carbonate (12.9 g, 36.6 mmol) were added, and refluxed to react for 18 h. After the reaction mixture was cooled to room temperature, the mixture was filtered though kieselguhr and evaporated, and purified by silica gel column chromatography (PE:acetone=4:1) to obtain compound 1 (7.4 g, 91.0%, white crystals). $^1$H NMR (300 MHz, CDCl$_3$) δ 8.63 (s, 1H), 8.13 (d, J=8.4 Hz, 2H), 7.91 (d, J=8.4 Hz, 2H), 3.94 (s, 3H), 1.27 (s, 9H). ESI-MS (m/z): 290.1[M+Na]$^+$.

Dimethylzinc (17 mL, 1 M in toluene, 17 mmol) was dissolved in 50 mL of re-distilled tetrahydrofuran, protected with N$_2$, and methyl magnesium bromide (15 mL, 1 M in THF, 15 mmol) was added dropwise at room temperature, and then the mixture was reacted at room temperature for 30 min. The reaction solution was cooled to −78° C., and a solution of compound 1 (2.67 g, 10 mmol) in tetrahydrofuran (15 mL) was slowly added dropwise, and then the reaction was carried out at −78° C. for 4 h. The reaction was quenched with saturated ammonium chloride solution and the reaction was extracted three times with ethyl acetate. The organic phases were mixed and washed with saturated brine, dried over anhydrous Na$_2$SO$_4$. After concentrated, it was purified by silica gel column chromatography (PE:acetone=5:1-4:1) to obtain compound H08-a (1.6 g, 56.5%, white solid). $^1$H NMR (300 MHz, CDCl$_3$) δ 8.01 (d, J=8.4 Hz, 2H), 7.42 (d, J=8.4 Hz, 2H), 4.59 (dq, J=6.6, 3.3 Hz, 1H), 3.91 (s, 3H), 3.44 (d, J=2.7 Hz, 1H), 1.52 (d, J=6.6 Hz, 3H), 1.23 (s, 9H). ESI-MS (m/z): 306.1[M+Na]$^+$.

The compound H08-a (1.18 g, 4.16 mmol) was dissolved in 5 mL of dichloromethane, and 10 mL of 2N HCl/MeOH solution was added dropwise under ice bath, and then the mixture was warmed to room temperature. After 3 h, TLC detected that the reaction was completed, and the resulting residue after concentration was put into saturated NaHCO$_3$ solution, extracted three times with dichloromethane. The mixed organic phase was washed with saturated brine, and dried over anhydrous Na$_2$SO$_4$. The crude compound H08-b (700 mg, 94.0%, yellow oil) was obtained after concentration without being further purified. $^1$H NMR (300 MHz, DMSO-d$_6$) δ 7.89 (d, J=8.1 Hz, 2H), 7.51 (d, J=8.1 Hz, 2H), 4.04 (q, J=6.6 Hz, 1H), 3.83 (s, 3H), 1.24 (d, J=6.6 Hz, 3H).

The preparation of the compound H08-c has been reported in the patent WO2012152208, and the synthesis step will not be described here in detail.

The compound H08-c (122 mg, 0.37 mmol) was dissolved in 2 mL of re-distallized dichloromethane, and 1108-b (80 mg, 0.45 mmol) and DMAP (67 mg, 0.56 mmol) were added and stirred for 10 min; under N$_2$ protection, EDCI (106 mg, 0.56 mmol) was added to the reaction mixture at 0° C., then the reaction was carried out overnight at room temperature. The reaction mixture was acidified with 1N hydrochloric acid and was extracted three times with ethyl acetate. The organic phases were mixed and washed with saturated brine, dried over anhydrous Na$_2$SO$_4$. After concentrated, it was purified by silica gel column chromatography (PE:acetone=6:1-4:1) to obtain compound H08-d (57 mg, 26.1%, yellow solid). $^1$H NMR (300 MHz, CDCl$_3$) δ 8.04 (d, J=8.1 Hz, 2H), 8.00 (s, 1H), 7.67 (d, J=7.8 Hz, 1H), 7.62 (dd, J=8.1, 1.2 Hz, 2H), 7.51 (d, J=8.1 Hz, 2H), 7.47-7.36 (m, 3H), 5.40-5.28 (m, 1H), 3.91 (s, 3H), 3.49-3.38 (m, 1H), 1.66 (d, J=7.2 Hz, 3H), 1.34-1.28 (m, 2H), 0.83-0.78 (m, 2H). ESI-MS (m/z): 490.1[M+H]$^+$.

The compound H08-d (57 mg, 0.12 mmol) was dissolved in 4 mL of methanol and 1 mL water, and lithium hydroxide monohydrate (50 mg, 1.2 mmol) was added and allowed to react overnight at room temperature. The pH was adjusted to 2-3 with 1 N hydrochloric acid, and a white solid was precipitated, filtered, and dried under vacuum at 40° C. to obtain the corresponding acid, which was directly used in the subsequent reaction without purification. The acid (41 mg, 0.084 mmol) was dissolved in 2 mL of re-distilling dichloromethane, and O-tert-butyldimethylsilylhydroxylamine (18 mg, 0.13 mmol) and DMAP (15 mg, 0.13 mmol) were added and stirred for 10 min; under N$_2$ protection, EDCI (24 mg, 0.13 mmol) was added to the reaction mixture at 0° C., then the reaction was carried out overnight at room temperature. The reaction mixture was diluted with ethyl acetate and the organic phase was washed three times with 1 N hydrochloric acid. At this time, the TBS was removed found by TLC, and the organic phase was washed with water and saturated brine, respectively, and dried over anhydrous Na$_2$SO$_4$. After concentrated, it was purified on silica gel column chromatography (CHCl$_3$:MeOH=25:1) to obtain compound H08 (29 mg, 70.4%, yellow solid). $[\alpha]_D^{25}$=+4433 (c 0.01, DMF). $^1$H NMR (300 MHz, DMSO-d$_6$) δ 11.16 (s, 1H), 9.00 (s, 1H), 8.63 (d, J=8.1 Hz, 1H), 8.40 (s, 1H), 7.80-7.72 (m, 4H), 7.55-7.39 (m, 5H), 5.25-5.16 (m, 1H), 3.29-3.20 (m, 1H), 1.56 (d, J=6.9 Hz, 3H), 1.31-1.24 (m, 2H), 0.83-0.77 (m, 2H). $^{13}$C NMR (125 MHz, DMSO-d$_6$) δ 164.2, 160.9, 158.3, 154.0, 153.3, 147.6, 144.6, 141.2, 140.2, 131.4, 130.2, 129.4, 129.1, 126.9, 126.6, 126.2, 47.9, 21.7, 13.8, 10.1. ESI-MS (m/z): 491.2[M+H]$^+$.

The following compounds can be obtained by route 1:

| Compound | Structural formula | $^1$H NMR and MS data |
|---|---|---|
| H01 | | $^1$H NMR (300 MHz, DMSO-d$_6$) δ 11.16 (s, 1H), 9.00 (s, 1H), 8.61 (d, J = 7.5 Hz, 1H), 8.01-7.92 (m, 2H), 7.72 (d, J = 7.8 Hz, 2H), 7.50 (d, J = 7.8 Hz, 2H), 5.26-5.13 (m, 1H), 3.27-3.17 (m, 1H), 1.55 (d, J = 6.9 Hz, 3H), 1.30-1.21 (m, 2H), 0.82-0.75 (m, 2H). ESI-MS(m/z): 415.1[M + H$^+$]. |
| H02 | | $^1$H NMR (300 MHz, DMSO-d$_6$) δ 11.17 (s, 1H), 9.01 (s, 1H), 8.63 (d, J = 8.4 Hz, 1H), 7.98 (s, 2H), 7.71 (d, J = 8.4 Hz, 2H), 7.50 (d, J = 8.4 Hz, 2H), 5.24-5.14 (m, 1H), 3.27-3.20 (m, 1H), 1.55 (d, J = 6.9 Hz, 3H), 1.29-1.20 (m, 2H), 0.81-0.75 (m, 2H). ESI-MS(m/z): 437.1 [M + Na]$^+$. |

| Compound | Structural formula | ¹H NMR and MS data |
|---|---|---|
| H03 | | ¹H NMR (300 MHz, DMSO-d₆) δ 11.17 (s, 1H), 9.01 (s, 1H), 8.64 (d, J = 8.1 Hz, 1H), 7.98 (s, 2H), 7.72 (d, J = 8.1 Hz, 2H), 7.50 (d, J = 8.1 Hz, 2H), 5.23-5.14 (m, 1H), 3.26-3.19 (m, 1H), 1.55 (d, J = 6.9 Hz, 3H), 1.29-1.21 (m, 2H), 0.81-0.75 (m, 2H). ESI-MS(m/z): 437.0[M + Na]⁺. |
| H04 | | ¹H NMR (300 MHz, DMSO-d₆) δ 11.15 (s, 1H), 9.00 (s, 1H), 8.52 (d, J = 8.7 Hz, 1H), 7.98 (s, 2H), 7.72 (d, J = 7.8 Hz, 2H), 7.51 (d, J = 7.8 Hz, 2H), 4.72 (t, J = 9.0 Hz, 1H), 3.20-3.10 (m, 1H), 2.35-2.22 (m, 1H), 1.28-1.19 (m, 2H), 1.02 (d, J = 6.0 Hz, 3H), 0.88-0.81 (m, 2H), 0.77 (d, J = 6.0 Hz, 3H). ESI-MS(m/z): 465.1[M + Na]⁺. |
| H05 | | ¹H NMR (300 MHz, CDCl₃) δ 7.69 (d, J = 8.4 Hz, 2H), 7.48 (s, 1H), 7.36 (d, J = 8.4 Hz, 2H), 5.27-5.16 (m, 1H), 3.42-3.29 (m, 1H), 2.51 (s, 3H), 1.56 (d, J = 4.2 Hz, 3H), 1.31-1.21 (m, 2H), 0.79-0.71 (m, 2H). ESI-MS(m/z): 429.1[M + H]⁺. |
| H06 | | ¹H NMR (300 MHz, CDCl₃) δ 7.71 (d, J = 8.4 Hz, 2H), 7.37 (d, J = 8.4 Hz, 2H), 6.98 (s, 1H), 5.34-5.17 (m, 1H), 3.43-3.30 (m, 1H), 2.47 (s, 3H), 1.56 (d, J = 4.2 Hz, 3H), 1.24-1.16 (m, 2H), 0.83-0.74 (m, 2H). ESI-MS(m/z): 429.2[M + H]⁺. |
| H07 | | ¹H NMR (300 MHz, CDCl₃) δ 9.71 (br s, 1H), 7.69 (d, J = 8.1 Hz, 2H), 7.50 (d, J = 7.8 Hz, 1H), 7.38 (d, J = 8.1 Hz, 2H), 5.32-5.17 (m, 1H), 2.81 (s, 4H), 1.88 (s, 4H), 1.56 (d, J = 6.9 Hz, 3H), 1.30-1.21 (m, 2H), 0.81-0.72 (m, 2H). ESI-MS(m/z): 469.3[M + H]⁺. |
| H09 | | ¹H NMR (300 MHz, CD₃OD + CDCl₃) δ 8.17 (d, J = 8.1 Hz, 1H), 8.01 (s, 1H), 7.75 (d, J = 8.1 Hz, 2H), 7.67-7.62 (m, 2H), 7.50 (d, J = 8.1 Hz, 2H), 7.16 (t, J = 8.4 Hz, 2H), 5.31-5.22 (m, 1H), 3.28-3.21 (m, 1H), 1.64 (d, J = 6.9 Hz, 3H), 1.30-1.25 (m, 2H), 0.84-0.78 (m, 2H). ESI-MS(m/z): 509.1 [M + H]⁺. |
| H10 | | ¹H NMR (300 MHz, DMSO-d₆) δ 10.21 (s, 1H), 8.57 (d, J = 8.4 Hz, 1H), 8.24 (s, 1H), 7.70 (t, J = 7.2 Hz, 4H), 7.49 (d, J = 6.9 Hz, 2H), 7.03 (d, J = 6.9 Hz, 2H), 5.23-5.12 (m, 1H), 3.79 (s, 3H), 3.03-2.97 (m, 1H), 1.54 (d, J = 6.6 Hz, 3H), 1.27-1.21 (m, 2H), 0.80-0.74 (m, 2H). |

| Compound | Structural formula | ¹H NMR and MS data |
|---|---|---|
| H11 | | ¹H NMR (300 MHz, DMSO-d₆) δ 11.16 (s, 1H), 8.99 (s, 1H), 8.62 (d, J = 7.8 Hz, 1H), 8.39 (s, 1H), 7.79-7.72 (m, 4H), 7.53-7.40 (m, 5H), 5.26-5.16 (m, 1H), 3.27-3.20 (m, 1H), 1.56 (d, J = 6.9 Hz, 3H), 1.31-1.23 (m, 2H), 0.83-0.75 (m, 2H). ESI-MS (m/z): 491.2[M + H]⁺. |

Preparation Example 2 (Compound No. H12-Route 2)

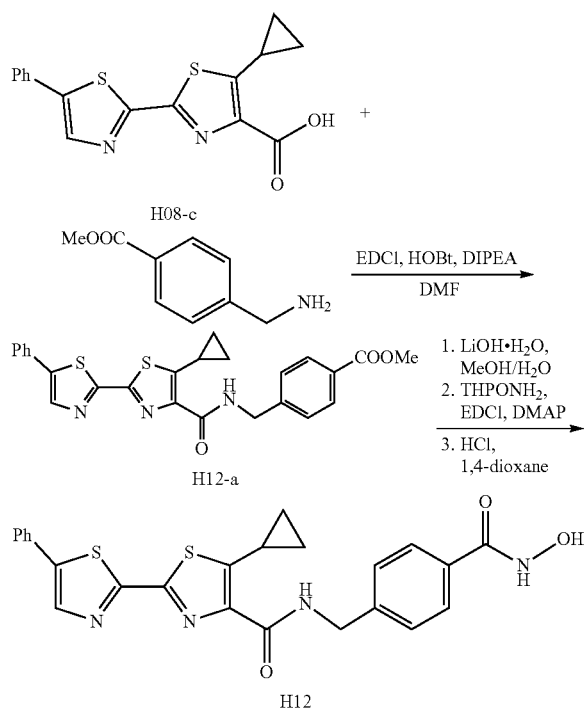

The compound H08-c (50 mg, 0.15 mmol), 4-aminomethylbenzoic acid methyl ester hydrochloride (45 mg, 0.22 mmol) and HOBt (30 mg, 0.22 mmol) were dissolved in 2 mL DMF. Diisopropylethylamine (38 mg, 0.29 mmol) was added, and the mixture was stirred at 0° C. for 10 min, then EDCI (34 mg, 0.18 mmol) was added and the reaction was allowed to warm and reacted overnight. The reaction solution was diluted with a large amount of water and extracted with EtOAc for three times. The mixed organic phase was washed with 1 N hydrochloric acid, saturated NaHCO₃ solution and saturated brine, and dried over anhydrous Na₂SO₄. After concentrated, it was purified by silica gel column chromatography (PE:acetone=3:1), and compound H12-a was obtained (25 mg, 35.2%, yellow solid). ¹H NMR (300 MHz, CDCl₃) δ 8.03 (d, J=8.7 Hz, 2H), 7.99 (s, 1H), 7.82 (t, J=6.9 Hz, 1H), 7.59 (d, J=8.1 Hz, 2H), 7.63-7.56 (m, 5H), 4.73 (d, J=6.3 Hz, 2H), 3.92 (s, 3H), 3.54-3.44 (m, 1H), 1.38-1.33 (m, 2H), 0.87-0.82 (m, 2H). ESI-MS (m/z): 476.1 [M+H]⁺.

The compound H12-a (25 mg, 0.052 mmol) was dissolved in 4 mL of methanol and 1 mL water, and lithium hydroxide monohydrate (22 mg, 0.52 mmol) was added and reacted at 80° C. for 3 h. The pH was adjusted to 2-3 with 1 N hydrochloric acid, and a yellow solid was precipitated. It was filtered and dried under vacuum at 40° C. to obtain the corresponding acid, which was directly used in next step reaction without purification. The acid (25 mg, 0.054 mmol) was dissolved in 2 mL of re-distilling dichloromethane, O-(tetrahydro-2H-pyran-2-yl)hydroxylamine (19 mg, 0.16 mmol) and DMAP (10 mg, 0.081 mmol) were added and stirred for 10 min; under N₂ protection, EDCI (15 mg, 0.078 mmol) was added to the reaction mixture at 0° C., then the reaction was carried out overnight at room temperature. After directly concentrated and purified by silica gel column chromatography (CHCl₃: MeOH=30:1), the crude product THP-protected hydroxamic acid was obtained. This crude product was dissolved in 2 mL of 1,4-dioxane, and 2 mL of 3 N hydrochloric acid was added, and stirred at room temperature for 15 min, and filtered to obtain compound H12 (10 mg, 38.9%, yellow solid). ¹H NMR (300 MHz, DMSO-d₆) δ 11.18 (s, 1H), 9.00 (s, 2H), 8.39 (s, 1H), 7.79-7.66 (m, 4H), 7.48-7.39 (m, 5H), 4.51 (d, J=6.3 Hz, 2H), 3.41-3.34 (m, 1H), 1.32-1.25 (m, 2H), 0.83-0.78 (m, 2H). ESI-MS (m/z): 499.1[M+Na]⁺.

Biological Experiment Examples

Experimental Example 1: Inhibition Activity Test of Histone Deacetylase 1, 3 and 6

1. Experimental Purpose:

The inhibitory activity of the example compounds against human histone deacetylases 1, 3 and 6 (i.e., human HDAC1, HDAC3 and HDAC6) was tested.

2. Experimental Materials:

The human HDAC1, HDAC3 and HDAC6 were all applied to the baculovirus expression system and purified by Dr. Li Jia et al. from the Shanghai Institute of Materia Medica.

Substrates: HDAC1, HDAC 3: Ac-Lys-Tyr-Lys (Ac)-AMC; HDAC6: Boc-lys (Ac)-AMC; all purchased from Shanghai Jill Biochemical Co., Ltd.

The 384 microplate was purchased from Perkin Elmer; and other common chemical reagents are domestic analytical pure (AR) reagents. The fluorescent signal detector Envision™ is a product of Perkin Elmer.

3. Experimental Method:

The activity of HDAC1 and HDAC3 was detected using Ac-Lys-Tyr-Lys(Ac)-AMC as substrate, and the activity of HDAC6 was detected using Boc-Lys(Ac)-AMC as substrate, and both were detected by fluorescence detection. After the substrate Ac-Lys-Tyr-Lys(Ac)-AMC and Boc-Lys (Ac)-AMC were deacetylated by HDAC, a fluorescent signal of the product AMC obtained by trypsin hydrolysis can be detected at 355 nm excitation light/460 nm emission light by the fluorescence signal detector Envision™. The initial velocity of the reaction is calculated by detecting the change in the fluorescence signal over time.

The test compound, enzyme and reaction buffer were well mixed and the substrate was added to start the reaction. After incubated for 24 h at room temperature, trypsin was added to react for 1 h, and finally the fluorescent signal is detected at 355 nm excitation light 460 nm emission light of fluorescence signal detector Envision™.

The following control groups were also set:
blank control group without enzyme,
solvent control in which DMSO was substituted for the test compound;
bexanostat positive control group;
CFH401 positive control group;
CFH455-C positive control group;
SAHA positive control group.

The final reaction volume was 50 μL. The specific reaction system was: 2% DMSO, 20-200 nM HDACs (HDAC1: 200 nM, HDAC3: 200 nM, HDAC6: 20 nM), 10 μM Ac-Lys-Tyr-Lys (Ac)-AMC, 50 μM Boc-lys (Ac)-AMC, 25 mM Hepes pH 8.0, 137 mM NaCl, 2.7 mM KCl, 4.9 mM $MgCl_2$, 0.1% BSA, 0.156% trypsin.

The fluorescence signal intensity at 460 nm was measured, and then the activity percentage (% Activity) of each concentration groups of the sample was calculated. The formula was as follows:

$$\% \text{ Activity} = \frac{\text{Compound fluorescence value} - \text{Enzyme free fluorescence value}}{\text{Negative control fluorescence value} - \text{Enzyme free fluorescence value}} \times 1\%$$

The logarithm of the concentration was plotted against the percentage of activity, and then the nonlinear regression was used to calculate the fit curve. The value of $IC_{50}$ was calculated by the software GraphPad Prism 5 formula log (inhibitor) vs. response—Variable slope.

Each of the above experiments was repeated 3 times, and there were more than 3 replicate wells for each experiment. The average $IC_{50}$ value of the three experiments was determined as the final indicator of the compound inhibition ability.

4. Experimental Results of Some Compounds:

TABLE 1

| ID | $IC_{50}$: nM | | |
|---|---|---|---|
| | HDAC1 | HDAC3 | HDAC6 |
| SAHA | 210.98 ± 114.33 | 232.08 ± 146.87 | 179.62 ± 85.59 |
| bexanostat | 95.14 ± 48.53 | 108.24 ± 59.72 | 67.82 ± 30.09 |
| CFH401 | 41.67 ± 7.48 | 30.33 ± 2.49 | 18.87 ± 0.01 |
| CFH455-C | 80.17 ± 15.38 | 75.16 ± 8.79 | 74.30 ± 41.76 |
| H01 | 80.98 ± 15.05 | 189.38 ± 16.72 | 41.65 ± 16.14 |
| H02 | 40.92 ± 0.41 | 42.51 ± 3.04 | 14.02 ± 1.74 |
| H04 | 38.25 ± 7.29 | 38.41 ± 7.13 | 14.15 ± 2.93 |
| H05 | 19.87 ± 0.47 | 17.06 ± 0.34 | 18.51 ± 0.45 |
| H06 | 16.52 ± 0.50 | 13.88 ± 0.31 | 19.08 ± 1.55 |
| H07 | 14.68 ± 0.67 | 11.35 ± 0.11 | 18.31 ± 0.84 |
| H08 | 2.53 ± 0.54 | 3.21 ± 0.60 | 2.89 ± 0.04 |
| H09 | 2.64 ± 0.02 | 2.54 ± 0.28 | 2.02 ± 0.10 |
| H10 | 3.57 ± 0.40 | 3.78 ± 0.93 | 2.38 ± 0.17 |

TABLE 1-continued

| ID | $IC_{50}$: nM | | |
|---|---|---|---|
| | HDAC1 | HDAC3 | HDAC6 |
| H11 | 42.96 ± 10.33 | 39.27 ± 8.54 | 31.73 ± 4.10 |
| H12 | 6.71 ± 0.11 | 6.15 ± 0.25 | 9.78 ± 0.02 |

It can be seen from the experimental results of table 1 that the compounds provided by the present invention have good inhibitory activity against HDAC1, 3, and 6: by only changing the linker (Linker) of bexanostat from the fatty long chain to benzyl, the present invention has improved the activity of each subtype of HDAC by 2-3 times than that of bexanostat. Based on that, a phenyl substitution was introduced to the 5-position of thiazole, which made the inhibitory activity of compound H12 on HDAC1, 3 and 6 even more improved than the previously reported (WO2012152208) compound CFH401 by 4-5 times, of which $IC_{50}$ was only about 6-10 nM; while the compound H08 obtained by introducing a chiral S-methyl group at the benzyl position continued to improve the HDAC enzyme inhibition activity, $IC_{50}$ of which can be reduced to 2-3 nM, which showed much higher activity than that of bexanostat.

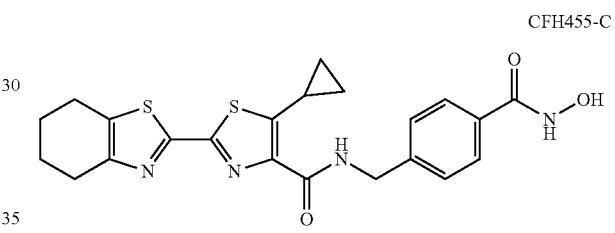

CFH455-C

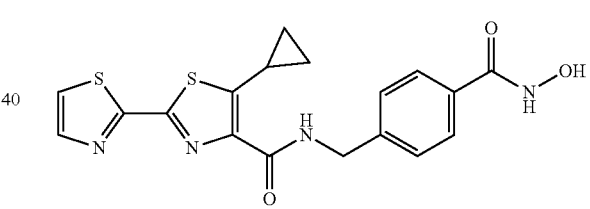

CFH401

Experimental Example 2: Cell Level Anti-Tumor Activity Test

1. Experimental Purpose:
The antitumor activity test of the example compounds was carried out, and the in vitro antitumor activities of the compounds were evaluated by measuring the growth inhibitory activities of the compounds against human multiple myeloma cell line 8266.

2. Experimental Materials:
CCK8 kit (Cat. CK04), purchased from Dongren Chemical Technology Co., Ltd.
96-well cell culture plates (Cat. 3599), purchased from Corning.
Absorbance microplate reader molecular devices, purchased from MD Corporation.
The RPMI 8226 cell line was obtained from Professor Hou Jian of Shanghai Changzheng Hospital, cultivated under culture conditions: RPMI-1640+10% FBS, routinely cultured in a saturated humidity incubator (Forma Scientific, Inc.) containing 5% $CO_2$ at 37° C.

3. Experimental Method:

According to the cell growth rate, the multiple myeloma cells in the logarithmic growth phase were inoculated into the 96-well culture plate at 100 μL/well, and then 1 μL/well of compound solution was added, and three replicate wells were set for each concentration, and the DMSO solvent control at corresponding concentration was also set. Multiple myeloma cells were cultured for 72 h at 37° C. and 5% $CO_2$. The RPMI 8226 cell was seeded at 5000/well density.

CCK-8 staining method: after the drug was applied, 10 μL of CCK-8 solution was added to each well, and incubated at 37° C. for 3 h. The OD value at 450 nm and 690 nm was measured by microplate reader.

4. Data Processing and Statistical Analysis:

The inhibition rate (% Inhibiton) and activity (% Activity) of the test substance on the proliferation of multiple myeloma cells were calculated according to the following formula, wherein $OD_{sample}$ refers to the absorbance value of the administration hole ($OD_{450}$-$OD_{690}$). OD DMSO refers to the absorbance of the DMSO control well ($OD_{450}$-$OD_{690}$).

$$\% \text{ Inhibition} = \left(1 - \frac{OD_{Sample}}{OD_{DMSO}}\right) \times 100$$

$$\% \text{ Activity} = \frac{OD_{Sample}}{OD_{DMSO}} \times 100$$

The logarithm of the concentration was plotted against the activity percentage (% Activity), and the fitted curve was calculated by nonlinear regression. The value of $IC_{50}$ was calculated by using the GraphPad Prism5 software log (inhibitor) vs response—Variable slope parameter setting. Each set of experiments was repeated three times independently, while 3 replicate wells per concentration.

5. Experimental Results of Some Compounds:

TABLE 2

| ID | $IC_{50}$: μM | ID | $IC_{50}$: μM |
|---|---|---|---|
| SAHA | 1.00 ± 0.35 | bexanostat | 0.69 ± 0.41 |
| H01 | 0.182 ± 0.015 | H02 | 0.028 ± 0.010 |
| H05 | 0.123 ± 0.043 | H06 | 0.050 ± 0.022 |
| H07 | 0.139 ± 0.019 | H08 | 0.008 ± 0.000 |
| H09 | 0.018 ± 0.006 | H10 | 0.012 ± 0.004 |
| H11 | 0.326 ± 0.018 | H12 | 0.008 ± 0.000 |

As can be seen from Table 2, the compounds provided by the present invention all exhibited good tumor cell proliferation-inhibiting activity, and the activity at the cellular level was increased by different extent when compared to bexanostat, and the activities of the compounds 1108 and H12 were improved by nearly one hundred times ($IC_{50}$ was around 8 nM), of which the result was consistent with the the enzyme level activity result.

Experimental Example 3: Cell Level Anti-Tumor Activity Test

1. Experimental Purpose:

The antitumor activity test of the example compounds was carried out, and the in vitro antitumor activities of the compounds were evaluated by measuring the growth inhibitory activities of the compounds against a plurality of human tumor cell lines.

2. Experimental Materials:

CCK8 kit (Cat. CK04), purchased from Dongren Chemical Technology Co., Ltd.

Sulfonhodamine B (SRB) protein staining method, purchased from sigma company.

96-well cell culture plates (Cat. 3599), purchased from Corning.

Absorbance microplate reader molecular devices, purchased from MD Corporation.

Source of cell lines:

TABLE 3

| Cell line | source | Culture conditions |
|---|---|---|
| Liver cancer BEL-7402 | SIBCB | 1640 + glucose + Ala + 10% G fetal calf serum |
| Liver cancer BEL-7404 | SIBCB | 1640 + glucose + Ala + 10% G fetal calf serum |
| Lung Cancer A549 | ATCC | F12 + Glu + 10% G fetal calf serum |
| Lung Cancer NCI-H1975 | ATCC | 1640 + Ala + 2.5 g/L glucose + 10% G fetal calf serum |
| Lung Cancer EBC-1 | JCRB | MEM + 10% G fetal calf serum |
| Breast Cancer MCF-7 | United States (Mongolia) | DMEM + 10% G fetal calf serum |
| Breast Cancer MDA-MB-231 | ATCC | L-15 + 10% G fetal calf serum |
| Breast Cancer T47D | Screening center | 1640 + 10% fetal calf serum |
| Stomach cancer NCI-N87 | ATCC | 1640 + Ala + 2.5 g/L glucose + 10% G fetal calf serum |
| stomach cancer MKN-74 | Japan | 1640 + 10% G fetal calf serum |
| colon cancer HT-29 | ATCC | 5A + 10% FBS |
| Embryonic lung cells MRC-5 | ATCC | EMEM + 10% fetal calf serum |
| lymphoma Ramos | Shanghai Cell Bank | RPMI-1640 + 10% G fetal calf |
| promyeloid leukemia HL60 | Shanghai Cell Bank | RPMI-1640 + 10% G fetal calf |
| Acute lymphoblastic leukemia MOLT-4 | JCRB | RPMI-1640 + 10% G fetal calf |
| Human blood lymphoma Raji | Shanghai Cell Bank | RPMI-1640 + 10% G fetal calf |
| Acute lymphocytic leukemia T lymphocyte CCRF | Shanghai Cell Bank | RPMI-1640 + 10% G fetal calf |
| lymphoma SU-DHL-6 | ATCC | RPMI-1640 + 10% G fetal calf |

Tumor cells (except MDA-MB-231) were routinely cultured under 37° C., 5% $CO_2$.

3. Experimental Method:

According to the cell growth rate, the tumor cells in the logarithmic growth phase were inoculated into 96-well culture plates at 90 μL/well, and adherently grown for 24 h and then added with 10 μL/well, and each concentration was set to three replicate wells, and DMSO vehicle controls and cell-free wells at corresponding concentration were also set. Tumor cells (except MDA-MB-231) were cultured for 72 h under conditions of 37° C. and 5% $CO_2$ (MDA-MB-231 cells were cultured at 37° C. without $CO_2$). After the drug was applied, 10 μL of CCK-8 solution was added to each well in Ramos, HL-60, Molt-4, Raji, CCRF-CEM, and SU-DHL-6 tumor cell line experiments, and incubated at 37° C. for 2 h. The OD value at 450 nm was measured by a microplate reader. In the BEL-7402, BEL-7404, A549, NCI-H1975, EBC-1, MCF-7, MDA-MB-231, T47D, NCI-$N_{87}$, MKN-74, HT-29 and MRC-5 tumor cell line experiments, the cell culture solution in the culture plate was discarded, and 10% (w/v) trichloroacetic acid (100 pt/well) was added and fixed at 4° C. for 1 h, and then rinsed with distilled water for five times. After dried by convert placing in an oven, the plate was taken out and 100 μL of SRB solution (4 mg/mL SRB powder dissolved in 1% glacial acetic acid) was added into each well. After standed at room temperature for 15 minutes, it was washed five times with 1% glacial acetic acid to completely remove the SRB which has not bounded to the plate protein. After dried by convert placing in an oven, 150 μL of 10 mM Tris solution was added into each well, and the OD value at 560 nm was measured by a microplate reader.

4. Data Processing and Statistical Analysis:

The inhibition rate of tumor cell proliferation was calculated according to the following formula. The half-inhibition amount $IC_{50}$ value was calculated by Log it method. Inhibition rate=(control group OD value−administration group OD value)/control group OD value×100%. Each set of experiments was repeated three times independently, while 3 replicate wells per concentration.

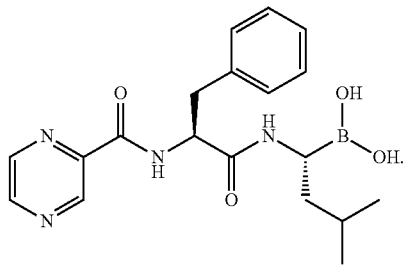 [SMILES: CC(C)C[C@H](NC(=O)[C@H](Cc1ccccc1)NC(=O)c1cnccn1)B(O)O]

3. Experimental Materials:

NOD/SCID mice, female, 5-6 weeks old, body weight 20±3 g, provided by Shanghai Lingchang Biotechnology

TABLE 4

| Cell line | $IC_{50}$ nM (mean ± SD) | | |
|---|---|---|---|
| | GCJ490-A | LBH589 | SAHA |
| Liver cancer BEL-7402 | 80.79 ± 2.49 | 21.28 ± 1.61 | 2775.86 ± 93.18 |
| Liver cancer BEL-7404 | 85.34 ± 22.87 | 18.55 ± 1.51 | 2809.75 ± 187.30 |
| Lung Cancer A549 | 142.60 ± 64.06 | 48.90 ± 7.01 | 2906.92 ± 678.09 |
| Lung Cancer NCI-H1975 | 66.38 ± 24.55 | 17.51 ± 2.23 | 1989.99 ± 301.56 |
| Lung Cancer EBC-1 | 109.91 ± 45.74 | 27.85 ± 1.72 | 1551.32 ± 474.44 |
| Breast Cancer MCF-7 | 58.52 ± 25.72 | 9.00 ± 0.94 | 883.37 ± 69.93 |
| Breast Cancer MDA-MB-231 | 76.56 ± 31.59 | 29.13 ± 0.42 | 3119.53 ± 434.29 |
| Breast CanceR T47D | 40.81 ± 16.76 | 6.98 ± 0.72 | 961.97 ± 111.70 |
| Stomach cancer NCI-N87 | 28.33 ± 8.67 | 8.42 ± 0.77 | 1075.17 ± 86.18 |
| stomach cancer MKN-74 | 106.43 ± 7.49 | 29.16 ± 0.97 | 3023.42 ± 253.09 |
| colon cancer HT-29 | 165.50 ± 6.57 | 37.55 ± 4.81 | 1331.41 ± 20.18 |
| Embryonic lung cells MRC-5 | 183.04 ± 18.35 | 76.93 ± 7.22 | 5099.39 ± 828.57 |
| lymphoma Ramos | 19.88 ± 6.40 | 7.14 ± 0.42 | 1616.73 ± 35.60 |
| promyeloid leukemia HL60 | 54.18 ± 36.62 | 12.30 ± 0.24 | 1115.33 ± 70.88 |
| Acute lymphoblastic leukemia MOLT-4 | 22.46 ± 15.89 | 15.02 ± 8.18 | 1208.44 ± 33.07 |
| Human blood lymphoma Raji | 20.63 ± 3.05 | 12.32 ± 1.61 | 1008.12 ± 37.87 |
| Acute lymphocytic leukemia T lymphocyte CCRF | 57.97 ± 33.58 | 13.72 ± 0.93 | 1530.30 ± 170.74 |
| lymphoma SU-DHL-6 | 11.41 ± 7.56 | 5.80 ± 0.34 | 787.46 ± 23.69 |

Experimental Example 3: Pharmacological Experiment of Compound H08 in Human Myeloma RPMI 8226 on NOD/SCID Mouse Transplantation Animal Model 1. Experimental Purpose:

The efficacy of compound H08 in an animal model of human multiple myeloma was investigated.

2. Dosing Regimen

TABLE 5

| Group | Tested compound | number of animals | Route of administration | Dosage | Dosing regimen |
|---|---|---|---|---|---|
| 1 | Solvent | 12 | p.o. | — | once/day, administrated for 3 weeks |
| 2 | PS341 | 6 | i.v. | 1 mg/kg | once/day, twice/week, (equivalent to only two days a week, and only once a day) for 3 weeks |
| 3 | bexanostat | 6 | p.o. | 100 mg/kg bid | twice/day, administrated for 3 weeks |
| 4 | H08 | 6 | p.o. | 50 mg/kg | once/day, administrated for 3 weeks |
| 5 | H08 | 6 | p.o. | 25 mg/kg | once/day, administrated for 3 weeks |

PS341: Bortezomib, a proteasome inhibitor, is used for the treatment of multiple myeloma, and the structure is as follows:

Co., Ltd., production certificate number: SCXK (Shanghai) 2013-0018. Number of animals per group: 6. IACUC number: 2013-0007 (Nanmo).

Human myeloma RPMI 8226 cell line was preserved by Li Jia et al., Shanghai Institute of Materia Medica. The cell line was inoculated to the right axillary fossa of NOD/SCID mice, and the amount of cells inoculated was $1\times10^7$ cells each mouse. After the transplanted tumor was formed, it was used in NOD/SCID mice after 2 passages.

4. Experimental Method:

The tumor tissue in the vigorous growth period was cut into 1.5 mm$^3$, and inoculated subcutaneously in the right axilla of the NOD/SCID mice under aseptic conditions. The diameter of the transplanted tumor of NOD/SCID mice were measured with a vernier caliper and the animals were randomly grouped when the tumor growed up to 100-300 mm$^3$. The grouping scheme is shown in Table 5, and the solvent control group was given an equal amount of blank solvent. The diameter of the transplanted tumor was measured twice a week during the entire experiment, and the body weight of the mice was weighed as well. The tumor volume (TV) was calculated as: TV=½×a×b$^2$, wherein a and b represent length and width, respectively. The relative tumor volume (RTV) was calculated based on the measured results and the formula was: RTV=$V_t/V_0$. Wherein $V_0$ is the tumor volume measured before grouping and dosing ($d_0$), and $V_t$ is the tumor volume at each measurement.

The evaluation indexes of antitumor activity were 1) relative tumor growth rate T/C (%), and the formula is as follows: T/C (%)=($T_{RTV}$/$C_{RTV}$)×100%, $T_{RTV}$ treatment group RTV; $C_{RTV}$: negative control RTV; 2) tumor volume growth inhibition rate GI %, and the formula is as follows: GI %=(1-(TVt-$TV_0$)/(CVt-$CT_0$))×100%, wherein TVt is the tumor volume measured in the therapeutic group at each time; $TV_0$ is the tumor volume measured in the therapeutic group when grouping and dosing; CVt is the tumor volume measured in the control group at each time; $CV_0$ is the tumor volume measured in the control group when grouping and dosing; 3) tumor weight inhibition rate was calculated as follows: tumor weight inhibition rate %=(Wc-$W_T$)/Wc× 100%, Wc: control group tumor weight, $W_T$: tumor weight of the therapeutic group.

5. Experimental Results:

FIG. 1 shows the pharmacodynamic results of compound H08 in human myeloma RPMI 8226 NOD/SCID mouse xenografts.

TABLE 6

| Group | body weight (g) $d_0$ | $d_{21}$ | TV ($mm^3$, average ± SD) $d_0$ | $d_{21}$ | RTV (Average ± SD) | T/C (%) |
|---|---|---|---|---|---|---|
| Solvent control p.o. | 22.0 ± 1.5 | 24.8 ± 1.5 | 154 ± 46 | 2,416 ± 831 | 15.88 ± 3.76 | |
| PS341 1 mg/kg, i.v. | 21.9 ± 1.0 | 23.3 ± 1.7 | 155 ± 48 | 1,077 ± 538 | 7.19 ± 3.58** | 45.27 |
| bexanostat 100 mg/kg bid, p.o. | 22.2 ± 1.4 | 19.8 ± 1.0 | 155 ± 46 | 620 ± 87 | 4.83 ± 0.51** | 30.40 |
| H08 50 mg/kg, p.o. | 22.2 ± 1.1 | 22.7 ± 0.9 | 154 ± 45 | 821 ± 406 | 5.48 ± 2.99** | 34.49 |
| H08 25 mg/kg, p.o. | 22.1 ± 1.3 | 23.7 ± 0.8 | 154 ± 44 | 1,279 ± 353 | 8.40 ± 1.35** | 52.89 |

(t student's test vs control, *p < 0.01)

It can be seen from FIG. 1 and Table 6 that the continuous oral administrating of compound H08 50 mg/kg for three weeks has a certain therapeutic effect on human myeloma RPMI 8226 NOD/SCID mouse xenografts, and can effectively inhibit the proliferation of mouse xenografts. The relative tumor proliferation rate T/C was 34.49%, which was equivalent to effect of oral administrating of bexanostat 100 mg/kg bid group (T/C was 30.40%), which was superior to the positive compound PS341.

All literatures mentioned in the present application are incorporated herein by reference, as though each one is individually incorporated by reference. Additionally, it should be understood that after reading the above teachings, those skilled in the art can make various changes and modifications to the present invention. These equivalents also fall within the scope defined by the appended claims.

The invention claimed is:

1. A compound of formula I or an optical isomer thereof, or a pharmaceutically acceptable salt thereof:

Formula I

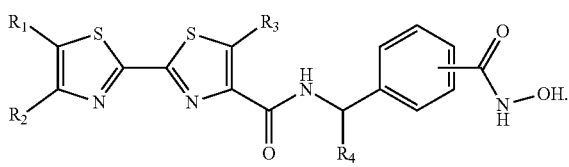

wherein, $R_1$ is selected from the group consisting of H, $C_1$-$C_6$ alkyl, $C_2$-$C_6$ alkenyl, $C_2$-$C_6$ alkynyl, $C_3$-$C_6$ cycloalkyl, and $C_5$-$C_{10}$ aryl; and $R_2$ is selected from the group consisting of $C_1$-$C_6$ alkyl, $C_2$-$C_6$ alkenyl, $C_2$-$C_6$ alkynyl, $C_3$-$C_6$ cycloalkyl, and $C_5$-$C_{10}$ aryl; or $R_1$ is selected from the group consisting of $C_1$-$C_6$ alkyl, $C_2$-$C_6$ alkenyl, $C_2$-$C_6$ alkynyl, $C_3$-$C_6$ cycloalkyl, and $C_5$-$C_{10}$ aryl; and $R_2$ is selected from the group consisting of H, $C_1$-$C_6$ alkyl, $C_2$-$C_6$ alkenyl, $C_2$-$C_6$ alkynyl, $C_3$-$C_6$ cycloalkyl, and $C_5$-$C_{10}$ aryl;

or $R_1$ and $R_2$ together with the carbon atom to which they are attached form a 5-7 membered saturated or partially saturated ring;

$R_3$ is selected from the group consisting of H, $C_1$-$C_6$ alkyl, $C_3$-$C_6$ cycloalkyl, $C_2$-$C_6$ alkenyl, $C_2$-$C_6$ alkynyl, and $C_5$-$C_{10}$ aryl; and $R_4$ is selected from the group consisting of $C_1$-$C_6$ alkyl, $C_3$-$C_6$ cycloalkyl, $C_2$-$C_6$ alkenyl and $C_2$-$C_6$ alkynyl;

wherein the $C_1$-$C_6$ alkyl, $C_3$-$C_6$ cycloalkyl, $C_2$-$C_6$ alkenyl, $C_2$-$C_6$ alkynyl, or $C_5$-$C_{10}$ aryl is unsubstituted or substituted with one or more groups selected from the group consisting of halogen, $C_1$-$C_6$ alkyl, halogenated $C_1$-$C_6$ alkyl, $C_2$-$C_6$ alkenyl, $C_2$-$C_6$ alkynyl, $C_1$-$C_6$ alkoxy, halogenated $C_1$-$C_6$ alkoxy, $C_3$-$C_6$ cycloalkyl, and $C_5$-$C_{10}$ aryl.

2. The compound or the optical isomer thereof, or the pharmaceutically acceptable salt thereof of claim 1, wherein, $R_1$ is H, $C_1$-$C_6$ alkyl, or $C_6$-$C_{10}$ aryl, and $R_2$ is $C_1$-$C_6$ alkyl or $C_6$-$C_{10}$ aryl; or $R_1$ is $C_1$-$C_6$ alkyl or $C_6$-$C_{10}$ aryl, and $R_2$ is H, $C_1$-$C_6$ alkyl, or $C_6$-$C_{10}$ aryl; or $R_1$ and $R_2$ together with the carbon atom to which they are attached form a 5, 6 or 7 membered partially saturated ring.

3. The compound or the optical isomer thereof, or the pharmaceutically acceptable salt thereof of claim 1, wherein, $R_3$ is $C_1$-$C_4$ alkyl, $C_6$-$C_{10}$ aryl substituted $C_1$-$C_4$ alkyl or $C_3$-$C_6$ cycloalkyl.

4. The compound or the optical isomer thereof, or the pharmaceutically acceptable salt thereof of claim 1, wherein, $R_4$ is $C_1$-$C_6$ alkyl.

5. A compound selected from the group consisting of:

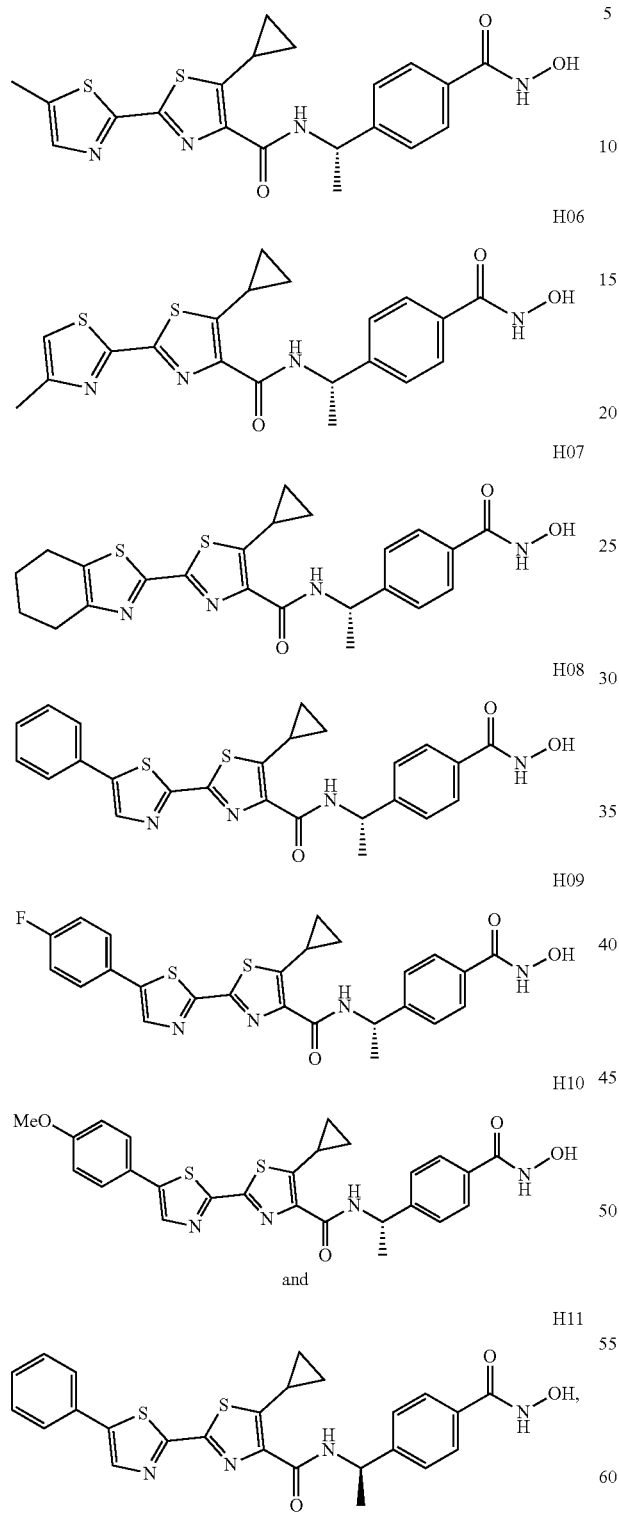

or an optical isomer thereof, or a pharmaceutically acceptable salt thereof.

6. A method for preparing the compound or the optical isomer thereof, or the pharmaceutically acceptable salt thereof of claim 1, wherein the compound is of formula II-1, $R_1$, $R_2$, and $R_3$ are defined as in claim 1, and $R_4$ is selected from the group consisting of $C_1$-$C_6$ alkyl, $C_3$-$C_6$ cycloalkyl, $C_2$-$C_6$ alkenyl and $C_2$-$C_6$ alkynyl,

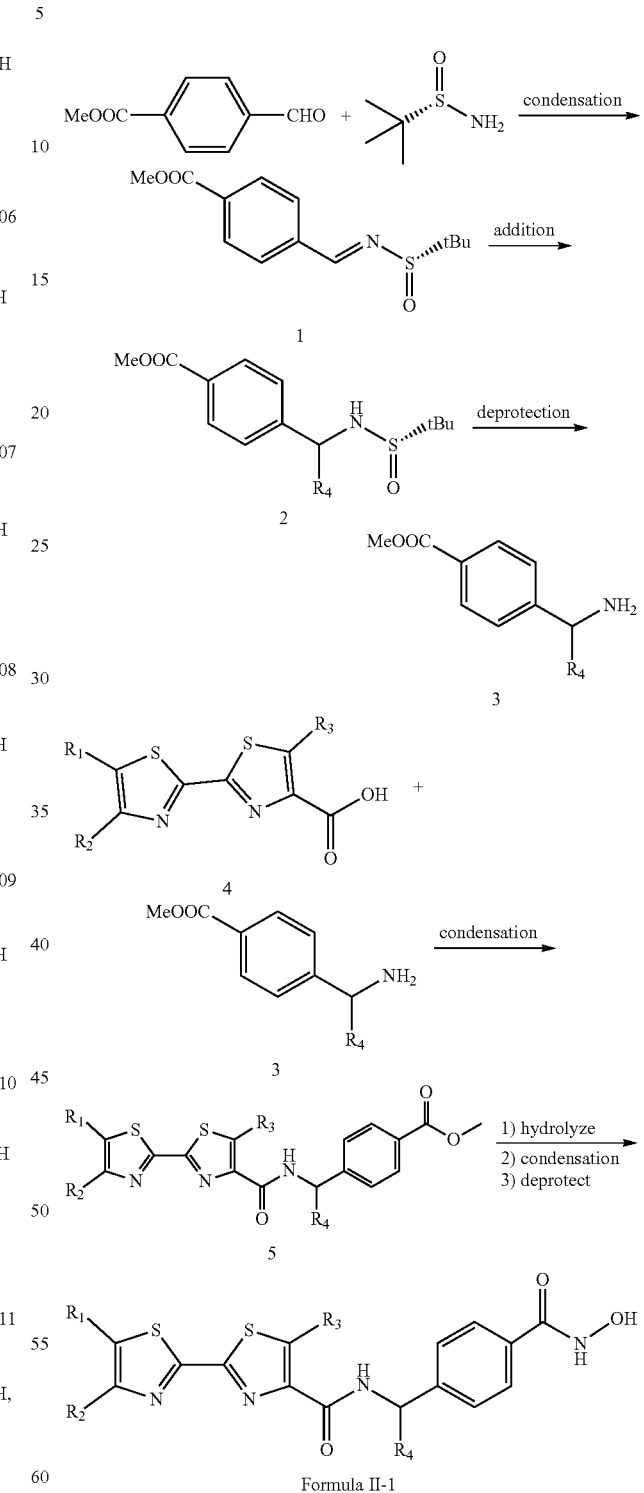

the method comprising:
(1) condensing methyl 4-acetylbenzoate with tert-butyl sulfenamide to form tert-butyl sulfoximine 1;
(2) reacting tert-butyl sulfinimide 1 with a Grignard reagent to form tert-butyl sulfenamide 2;

(3) deprotecting tert-butyl sulfinamide 2 to form amine 3;
(4) condensing amine 3 with acid 4 to form methyl ester 5; and
(5) reacting methyl ester 5 with alkali to form a hydrolysis product, reacting the hydrolysis product with a hydroxylamine protected by a protecting group to form a condensation product protected by the protecting group, and removing the protecting group to form the compound of formula II-1; or wherein the compound is of formula II-2, $R_1$, $R_2$, and $R_3$ are defined as in claim 1,

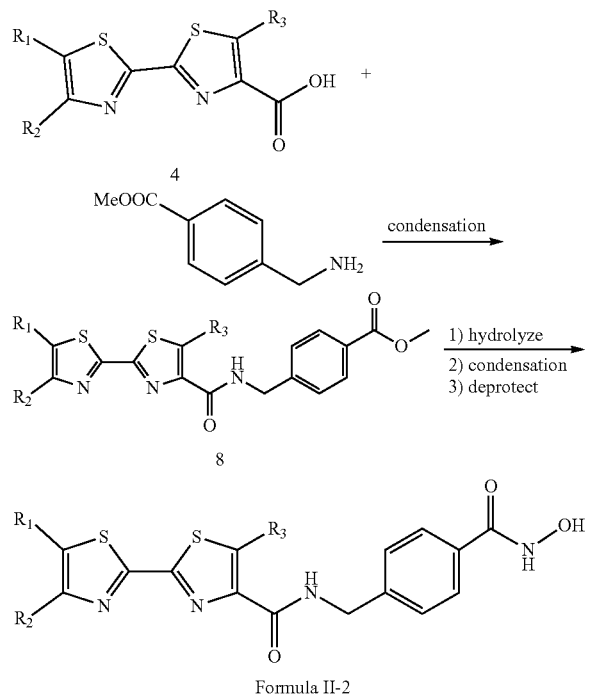

Formula II-2 or the method comprising:
(i) reacting acid 4 with methyl 4-aminomethylbenzoate to form methyl ester 8;
(ii) reacting methyl ester 8 with alkali to form a hydrolysis product, reacting the hydrolysis product with a hydroxylamine protected by a protecting group to form a condensation product, and removing the protecting group to form the compound of formula II-2.

7. A pharmaceutical composition, wherein the pharmaceutical composition comprises a therapeutically effective amount of the compound or the optical isomer thereof, or the pharmaceutically acceptable salt thereof of claim 1, and pharmaceutically acceptable carriers.

8. A method of inhibiting a histone deacetylase in a subject in need thereof comprising administering to the subject an effective amount of the compound or the optical isomer thereof, or the pharmaceutically acceptable salt thereof according to claim 1.

9. A method of inhibiting tumor cells or a tumor in a subject in need thereof comprising administering to the subject an effective amount of the compound or the optical isomer thereof, or the pharmaceutically acceptable salt thereof according to claim 1.

10. A method of claim 9, wherein the tumor cells are multiple myeloma cells, colon cancer cells, lung cancer cells, embryo lung cells, liver cancer cells, breast cancer cells, ovarian cancer cells, pancreatic cancer cells, rectal cancer cells, gastric cancer cells, lymphoma cells or leukemia cells; and the tumor is multiple myeloma, colon cancer, lung cancer, liver cancer, breast cancer, ovarian cancer, pancreatic cancer, rectal cancer, gastric cancer, lymphoma, or leukemia.

11. A pharmaceutical composition, wherein the pharmaceutical composition comprises a therapeutically effective amount of the compound or the optical isomer thereof, or the pharmaceutically acceptable salt thereof of claim 5, and pharmaceutically acceptable carriers.

12. A method of inhibiting a histone deacetylase in a subject in need thereof comprising administering to the subject an effective amount of the compound or the optical isomer thereof, or the pharmaceutically acceptable salt thereof according to claim 5.

13. A method of inhibiting tumor cells or a tumor in a subject in need thereof comprising administering to the subject an effective amount of the compound or the optical isomer thereof, or the pharmaceutically acceptable salt thereof according to claim 5.

14. A method of claim 13, wherein the tumor cells are multiple myeloma cells, colon cancer cells, lung cancer cells, embryo lung cells, liver cancer cells, breast cancer cells, ovarian cancer cells, pancreatic cancer cells, rectal cancer cells, gastric cancer cells, lymphoma cells or leukemia cells; and the tumor is multiple myeloma, colon cancer, lung cancer, liver cancer, breast cancer, ovarian cancer, pancreatic cancer, rectal cancer, gastric cancer, lymphoma, or leukemia.

15. A compound selected from the group consisting of:

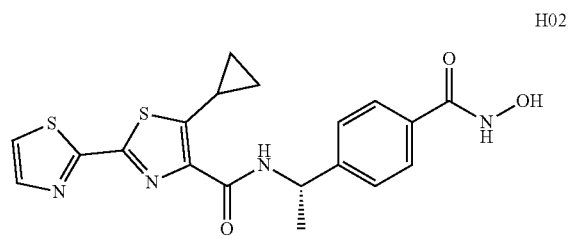 [SMILES: C[C@H](NC(=O)c1nc(-c2nccs2)sc1C1CC1)c1ccc(C(=O)NO)cc1]

H02 and

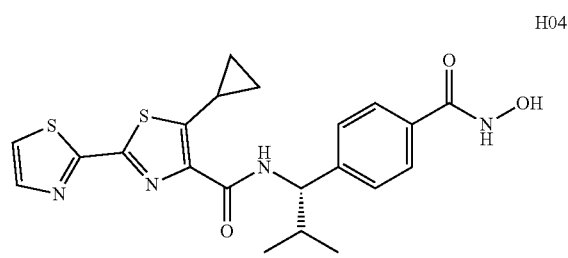 [SMILES: CC(C)[C@H](NC(=O)c1nc(-c2nccs2)sc1C1CC1)c1ccc(C(=O)NO)cc1]

H04 an optical isomer thereof, or a pharmaceutically acceptable salt thereof.

16. A pharmaceutical composition comprising an effective amount of the compound, the optical isomer, or the pharmaceutically acceptable salt thereof of claim 15, and a pharmaceutically acceptable carrier.

17. A method of inhibiting a histone deacetylase in a subject in need thereof comprising administering to the subject an effective amount of the compound, the optical isomer, or the pharmaceutically acceptable salt thereof according to claim 15.

18. A method of inhibiting tumor cells or a tumor in a subject in need thereof comprising administering to the subject an effective amount of the compound, the optical isomer, or the pharmaceutically acceptable salt thereof according to claim 15.

19. A method of claim 18, wherein the tumor cells are multiple myeloma cells, colon cancer cells, lung cancer cells, embryo lung cells, liver cancer cells, breast cancer cells, ovarian cancer cells, pancreatic cancer cells, rectal cancer cells, gastric cancer cells, lymphoma cells or leukemia cells; and the tumor is multiple myeloma, colon cancer, lung cancer, liver cancer, breast cancer, ovarian cancer, pancreatic cancer, rectal cancer, gastric cancer, lymphoma, or leukemia.

* * * * *